US00PP33801P2

(12) United States Plant Patent
Hansen

(10) Patent No.: US PP33,801 P2
(45) Date of Patent: Dec. 28, 2021

(54) ***SALVIA* PLANT NAMED 'TIDAL POOL'**

(50) Latin Name: *Salvia nemorosa*
Varietal Denomination: Tidal Pool

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/300,430

(22) Filed: Jun. 29, 2021

(51) Int. Cl.
*A01H 5/02* (2018.01)
*A01H 6/50* (2018.01)

(52) U.S. Cl.
USPC ..... Plt./475

(58) Field of Classification Search
USPC ..... Plt./475
See application file for complete search history.

*Primary Examiner* — Susan McCormick Ewoldt

(57) ABSTRACT

The new and distinct cultivar of perennial *Salvia* plant named 'Tidal Pool' characterized by its large, violet-blue flowers with lighter blue interiors from dark violet-blue buds and calyxes strongly blushed with dark greyed-red, densely arranged in verticils. The new plant has a medium height, compact, rounded, low, broad habit with stiff, heavily-branched stems and a strong vigorous growth rate and gray-green foliage. 'Tidal Pool' is useful for landscaping as a specimen plant or en masse.

1 Drawing Sheet

Botanical denomination: *Salvia nemorosa.*
Cultivar designation: 'Tidal Pool'.

STATEMENT REGARDING PRIOR DISCLOSURES UNDER 37 CFR 1.77(b)(6)

The first non-enabling disclosure of the new plant, in the form of a photograph and brief description was in website managed by Walters Gardens, Inc. on Feb. 1, 2020 followed by the "Walters Gardens 20-21 Catalog" first distributed on May 20, 2020. The claimed plant was first sold on Jun. 29, 2020 by Walters Gardens, Inc., who obtained the new plant and all information relating thereto from the inventor. No plants of *Salvia* 'Tidal Pool' have been sold in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of perennial *Salvia* plant hereinafter referred to by the cultivar name *Salvia* 'Tidal Pool' or as the new plant. The new plant was from a cross between 'Azure Snow' U.S. Plant Pat. No. 30,534 and 'Crystal Blue' U.S. Plant Pat. No. 26,344 on Jun. 20, 2015 at a wholesale perennial nursery in Zeeland, Mich., USA. Seed was collected in the summer of 2015 and sown at the same nursery. The new plant was initially evaluated in the summer of 2016 and assigned the breeder code 15-24-5 through the trial process prior to assigning a cultivar name.

The new *Salvia* was further evaluated and asexually propagated initially by division and later by basal cuttings taken at the same nursery in Zeeland, Mich., USA in 2017. Evaluation of these and further cutting grown plants shows that *Salvia* 'Tidal Pool' continues to be stable and produce true to type plants in successive generations of asexual propagation.

SUMMARY OF THE INVENTION

Plants of *Salvia* 'Tidal Pool' have not been observed under all possible environmental conditions. The phenotype may vary somewhat with variations in environment such as temperature, nutrition and light intensity without, however, any variance in genotype.

'Tidal Pool' can be closely compared to 'Blue Hill' (not patented), 'May Night' (not patented), 'Violet Profusion' U.S. Plant Pat. No. 31,467, 'Indiglo Girl' U.S. Plant Pat. No. 31,254, 'Midnight Model' U.S. Plant Pat. No. 29,498 and 'Violet Riot' U.S. Plant Pat. No. 26,273.

'Blue Hill' has similar height but narrower in width with less branching of the peduncles and the flower color is a lighter bluish-violet. 'May Night' has a more upright habit with smaller flowers per inflorescence of deep violet-purple. 'Violet Profusion' has flowers that are violet-blue with rosy-purple calyxes with a shorter habit. 'Indiglo Girl' has slightly taller habit and flowers of indigo-blue with dark calyxes. 'Midnight Model' has flowers that are more violet-blue with a slightly larger and less rounded habit. 'Violet Riot' has more compact flowering of vivid violet-blue flowers on taller inflorescences.

The female parent, 'Azure Snow' has similar height, but the flowers are larger and bicolor with deep violet-blue and white. The male parent, 'Crystal Blue', has a similar habit to the new plant, but the flowers are light sky-blue.

The following characteristics in combination distinguish *Salvia* 'Tidal Pool' as a new and distinct cultivar from all other cultivars known to the inventor:

1. Large, violet-blue flowers with lighter blue interiors densely arranged in verticils;
2. Stiff, low, broad, rounded, habit of heavily-branched stems;

3. Dark violet-blue flower buds and calyxes strongly blushed with dark greyed-red;
4. Medium height, compact, strong, vigorous and winter-hardy habit;
5. Rugose gray-green foliage.

BRIEF DESCRIPTION OF THE DRAWINGS

The photographs of the new plant demonstrate the unique traits and the overall appearance of *Salvia* 'Tidal Pool'. The colors are as accurate as reasonably possible with color reproductions. Variation in ambient light spectrum, source and direction may cause the appearance of minor variation in color. The plant used in the photographs was a three-year-old plant grown in an open, full-sun trial garden at a wholesale perennial nursery in Zeeland, Mich. with supplemental water and fertilizer when needed.

DETAILED BOTANICAL DESCRIPTION

Figure 1:
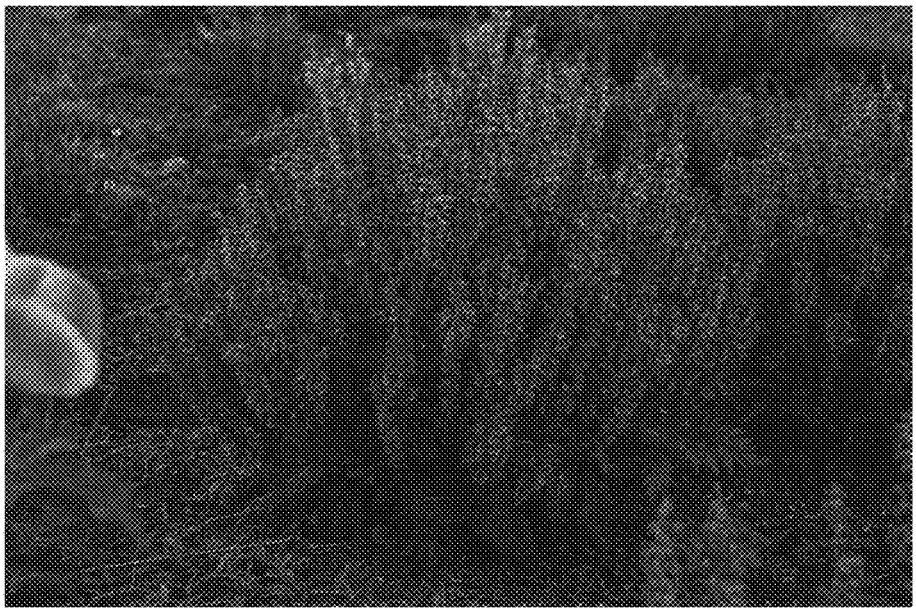
FIG. 1 shows the plant habit in full flower in a landscape.
Figure 2:
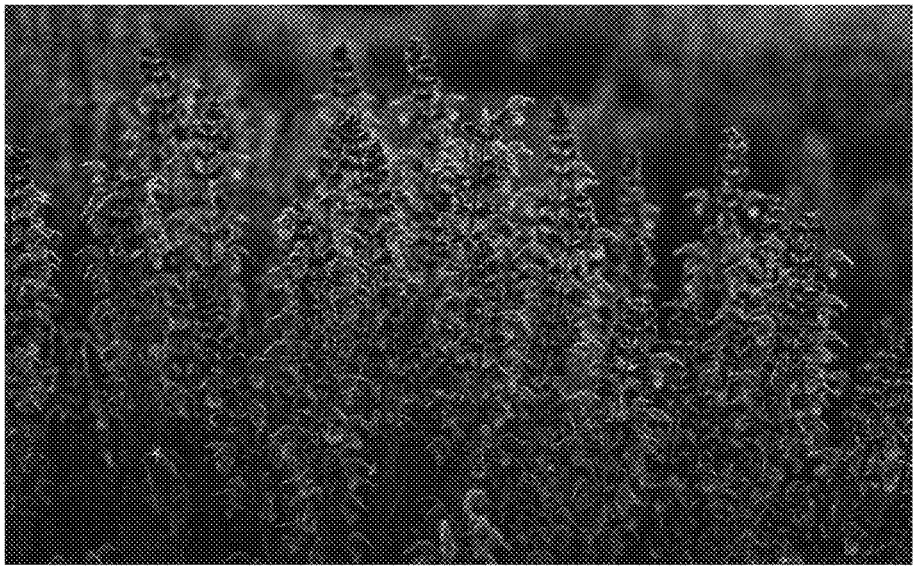
FIG. 2 shows a close-up of the flower scape with the buds, flowers, stems and calyxes.

The following descriptions and color references except where common dictionary terms are used are based on the 2015 edition of The Royal Horticultural Society Colour Chart. *Salvia* 'Tidal Pool' has not been observed under all possible environments. The phenotype may vary slightly with different growing environments such as temperature, light, fertility, soil pH, moisture and plant maturity levels, but without any change in the genotype. The following observations and size descriptions are based on two-year old plants growing in an outdoor full-sun trial garden at a wholesale perennial nursery in Zeeland, Mich. Plants were given supplemental water and fertilizer and plant growth regulators were used for the greenhouse trials only.

Botanical classification: *Salvia nemorosa;*

Parentage: Female or seed parent was 'Azure Snow'; male or pollen parent 'Crystal Blue';

Plant habit: Winter-hardy herbaceous perennial; multi-stemmed, compact, rounded, with mostly basal foliage, and flowers in several tightly arranged verticils on branched upright racemes displayed above foliage; in flower with panicles to about 47 cm tall and about 76 cm wide at the fullest point; cauline foliage extends up the stems about 22 to 29 cm; about 24 to 34 flowering panicles per plant;

Propagation: By basal vegetative shoot cuttings; time to produce a rooted stems about two weeks;

Growth rate: Rapid, vigorous, finishing in a 65 mm container in about 7 weeks from rooted cutting, and from 65 mm container to flowering 3.8 liter container in about 8 weeks;

Root description: Fine, well-branched; color dependent on age and soil type, from cream to dark tan in color;

Foliage: Opposite; simple; slightly rugose; lanceolate; margin irregularly crenate and sparsely ciliolate; adaxial surface glabrous, and abaxial puberulent; acute apex and base cordate to truncate; leaf blades about 12.5 cm long and 5.5 cm across, decreasing in size distally; average about 10.5 cm long and 4.5 cm across; faint sage fragrance;

Foliage color: Young adaxial surface nearest RHS 137B, young abaxial surface between RHS 138A and RHS 138B; mature adaxial between 137A and RHS 137B, mature abaxial nearest RHS 137B;

Venation: Reticulate; impressed on adaxial side and costate on abaxial side; pubescent abaxial, micro-puberulent adaxial;

Vein color: Adaxial midrib nearest RHS 145D; adaxial primary and secondary veins nearest RHS 137B; abaxial midrib nearest RHS 148D; abaxial primary veins nearest RHS 148C and secondary veins gradually darkening to nearest RHS 146B toward leaf margin;

Petiole: Slightly concavo-convex; pubescent to glandular; to about 5.0 cm long and 5.0 mm wide, average 4.0 cm long and 4.0 mm wide at base, decreasing distally;

Petiole color: Adaxial nearest RHS 146B along margins and center nearest RHS 145D; abaxial margins nearest 138A and center nearest RHS 145C; without significant anthocyanins;

Flower description: Perfect; bilabiate; zygomorphic; fused corolla portion glabrous adaxial and puberulent abaxial;

Flower size: 16.0 mm long to tip of exserted stigma, 8.0 mm tall, 6.0 mm wide; corolla 13.0 mm long, 8.0 mm tall and 6.0 mm wide; corolla fused basal portion 6.0 mm long, 4.0 mm tall and 2.5 mm wide;

Inflorescence: Panicle; upright with upright branches at about 80° angle above horizontal, rarely compound branched; branches to 28 cm long and 3.0 mm across base; flowering portion 22 cm tall and 12 cm across with branches; verticillate with flowering generally beginning at lower verticils and advancing up the scape, but not all flowers at each verticil opening at the same time giving the effect of a scape being in continuous flower for longer periods; typically six flowers per verticil; average distance between verticils about 9.0 mm, greater proximally and less distally; about 16 verticils per plant; about 200 to 300 flowers per branched panicle;

Flowering period: Flowering beginning late spring for about six weeks and repeating if initial inflorescences removed;

Peduncle: Quadrangular; pubescent to glandular; to 40.0 mm long and 5.0 mm across at base;

Peduncle color: Between RHS 146A and RHS 138A;

Flower attitude: Flower midline projected about 10 degree angle above horizontal and hood petal about 30 degree angle above horizontal;

Flower longevity: About four days on the plant or as cut flower; self-cleaning, petals not persistent;

Flower fragrance: None detected under present growing conditions;

Flower buds one day prior to anthesis: Arcuate dorsally, flat ventrally and flattened slightly laterally; with rounded apex; puberulent to glandular; about 9.5 mm long, 4.0 mm tall and 2.0 mm wide;

Bud color: Exposed dorsal hood blend between RHS 93A and RHS 93B and ventral labium nearest RHS N88C; abaxial calyx nearest RHS 138A, with veins and strong blushing dorsally nearest RHS 187A;

Petals: Bilabiate corolla; upper hood lip and lower lip (labium) with three lobes;

Hood (upper) petal: Glandular abaxial, glabrous adaxial; about 13.0 mm long, 4.0 mm tall and 2.0 mm across; folded along longitudinal axis; apex rounded and emarginate, with 1.5 mm deep notched apex and base fused with labium in proximal 6.0 mm;

Hood color: Adaxial between RHS 93B and RHS N88A, abaxial nearest RHS N88B;

Labium (lower) petal: Consisting of three lobes, two proximal side lobes and larger center lobe;

*Center lobe.*—Obcordate, cupped; truncate emarginate apex with notch about 1.0 mm deep; margin slightly crenulate; puberulent in center 3 mm of abaxial base before tube, glabrous adaxial and distal abaxial; size about 10 mm long (including fuse base) extending 4 mm beyond fusion point; natural width 5 mm and when spread to 6 mm.

Center lobe color: Adaxial nearest RHS 93A and abaxial nearest RHS 93A;

Side lobes: Lanceolate; apices rounded; base fused to corolla tube; revolute; puberulent to glandular abaxial and glabrous adaxial; size about 1.5 mm long from fusion and 1.0 mm wide;

Side lobes color: Nearest RHS 93A adaxial and abaxial;

Androecium: Two, fused with labium, contained within hood petal except when triggered by pollinator;

*Filament.*—Glabrous, fused in proximal 13.0 mm from base of labium; arcuate around inside of hood petal; about 9.0 mm long beyond fusion and less than 0.5 mm diameter with 2.0 mm long trip mechanism longitudinally folded at base; color of filament nearest RHS 84D; color of trip mechanism base and center nearest RHS 84D.

*Anther.*—Glabrous; oblong ellipsoidal; dorsifixed; longitudinal; about 1.0 mm long and 5.0 mm diameter; color nearest RHS N192A.

*Pollen.*—Abundant; less than 0.1 mm circumference; color nearest RHS 13B.

Gynoecium: One, arcuate around inside of hood petal;

*Style.*—Exserted; about 17.0 mm long and 0.5 mm diameter; color in distal 2.0 mm nearest RHS 86D and below nearest RHS 84D.

*Stigma.*—Bifurcate and curved in the terminal 2.0 mm; about 0.3 mm diameter; apex acute; color nearest RHS 86A.

*Ovary.*—Superior; four seeded; color nearest RHS 145D.

Fruit: Nutlet, one to four per flower; globose; about 1.6 mm diameter; color between RHS 200A and RHS 202A;

Calyx: Campanulate; fused in basal 4.0 mm; tube about 7.0 mm long and 3.0 mm tall at mouth and 2.0 mm wide; lower set bifurcate in distal 2.0 mm; upper set of trifurcate in distal 1.0 mm;

Sepals: Five, three upper and two lower; linear; acute apex; fused in basal 4.0 mm;

Sepal color: Adaxial proximal 3 mm nearest RHS 137C with veins nearest RHS 137C, distal portion nearest RHS 138A; abaxial nearest RHS 138A, in high light exposure with veins of and dorsally strongly blushed with nearest RHS 187A;

Bracts: Each verticil subtended by two opposite deltoid bracts; apex narrowly acute, base sessile and truncate, margin crenate; glabrous adaxial and puberulent abaxial; bract size up to 33 mm long and 16.0 mm wide, decreasing distally;

Bract color: Adaxial surfaces nearest RHS 137A with midrib nearest RHS 145D, abaxial nearest RHS 137A with midrib nearest RHS 145D; without significant anthocyanins;

Pedicels: Cylindrical; puberulent to glandular; to about 3 mm long and 1 mm diameter; projecting at about a 45 degree angle at flower anthesis;

Pedicel color: Between RHS 186C and RHS 138B;

Culture: Plants of *Salvia* 'Tidal Pool' perform best with adequate moisture and good drainage and are hardy from USDA zone 3 to 8.

Disease and pest resistance: Resistant to diseases and pests beyond that common to *Salvia* has not been noted.

It is claimed:

1. The new and distinct perennial *Salvia* plant named 'Tidal Pool' as herein described and illustrated.

* * * * *